United States Patent
Mauracher et al.

(10) Patent No.: US 11,262,297 B2
(45) Date of Patent: Mar. 1, 2022

(54) SUBSTRATE FOR FLUORESCENCE AMPLIFICATION

(71) Applicants: Fianostics GmbH, Wiener Neustadt (AT); STRATEC Consumables GmbH, Anif (AT)

(72) Inventors: Christoph Mauracher, Salzburg (AT); Georg Bauer, Salzburg-Aigen (AT); Adrian Prinz, Bad Reichenhall (DE); Gottfried Aichinger, Hallein (AT); Gerhard Hawa, Vienna (AT)

(73) Assignees: FIANOSTICS GmbH, Wiener Neustadt (AT); STRATEC Consumables GmbH, Anif (AT)

( * ) Notice: Subject to any disclaimer, the term of this patent is extended or adjusted under 35 U.S.C. 154(b) by 535 days.

(21) Appl. No.: 15/759,347

(22) PCT Filed: Sep. 16, 2016

(86) PCT No.: PCT/EP2016/071953
§ 371 (c)(1),
(2) Date: Mar. 12, 2018

(87) PCT Pub. No.: WO2017/046320
PCT Pub. Date: Mar. 23, 2017

(65) Prior Publication Data
US 2018/0195956 A1 Jul. 12, 2018

(30) Foreign Application Priority Data
Sep. 16, 2015 (AT) .................. A50793/2015

(51) Int. Cl.
| | |
|---|---|
| *G01N 21/00* | (2006.01) |
| *G01N 21/3563* | (2014.01) |
| *B82Y 30/00* | (2011.01) |
| *G01N 21/64* | (2006.01) |
| *G01N 33/543* | (2006.01) |
| *B82Y 35/00* | (2011.01) |
| *G01N 15/14* | (2006.01) |
| *G01N 15/06* | (2006.01) |

(52) U.S. Cl.
CPC .......... *G01N 21/3563* (2013.01); *B82Y 30/00* (2013.01); *B82Y 35/00* (2013.01); *G01N 15/147* (2013.01); *G01N 21/648* (2013.01); *G01N 21/6428* (2013.01); *G01N 21/6452* (2013.01); *G01N 21/6458* (2013.01); *G01N 33/54366* (2013.01); *G01N 2015/0668* (2013.01); *G01N 2021/6482* (2013.01)

(58) Field of Classification Search
CPC ........................ G01N 21/6428; G01N 15/1484
USPC ................................................. 436/172, 164
See application file for complete search history.

(56) References Cited

U.S. PATENT DOCUMENTS

| | | | |
|---|---|---|---|
| 2005/0214841 A1 | 9/2005 | Nakamura | |
| 2009/0262640 A1 | 10/2009 | Takahashi et al. | |
| 2010/0118390 A1* | 5/2010 | Blair | G02B 5/008 |
| | | | 359/346 |
| 2013/0065777 A1* | 3/2013 | Altug | G01N 33/553 |
| | | | 506/9 |

FOREIGN PATENT DOCUMENTS

| | | |
|---|---|---|
| WO | 2007/094817 A2 | 8/2007 |
| WO | 2009/059204 A1 | 5/2009 |

OTHER PUBLICATIONS

Liu, Y. et al., 'Biosensing based upon molecular confinement in metallic nanocavity arrays,' Institute of Physics Publishing, Nanotechnonlgy 15, (2004) (8 pages).
Liu, Y. et al., 'Fluorescence enhancement from an array of subwavelength metal apertures,' Optical Society of America, Optic Letters, vol. 28, No. 7, (Apr. 1, 2003) (3 pages).
Liu, Y. et al., 'Fluorescence enhancement from a Periodic Array of Sub-Wavelength Metallic Cavities,' OSA/IPR, (2003) (4 pages).
Schmidt, T.M., et al., 'Plasmonic Fluorescence Enhancement of DBMBF2 Monomers and DBMBF2—Toluene Exciplexes using Al-Hole Arrays,' American Chemical Society, The Journal of Physical Chemistry, (2014) (8 pages).
Chou, S.Y., et al., 'Nanoimprint lithography,' American Vacuum Society, J. Vac. Sci. Technol. B 14(6), (Nov. 12, 1996) (6 pages).
Lordan, F., et al., 'Effect of Cavity Architecture on the Surface-Enhanced Emission from Sire-Selective Nanostructured Cavity Arrays,' American Chemical Society, The Journal of Physical Chemistry, (2011) (5 pages).
Brolo, A.G., et al., 'Enhanced Fluorescence from Arrays of Nanoholes in a Gold Film,' American Chemical Society, J. Am. Chem. Soc., (2005) (6 pages).
Written Opinion for PCT/EP2016/071953 (7 pages).
English Translation of Written Opinion for PCT/EP2016/071953 (6 pages).
Gartia, M.R. et al., 'Colorimetric Plasmon Resonance Imaging Using Nano Lycurgus Cup Arrays,' Adv. Optical Mater. 2013, pp. 68-76 (10 pages).
Seo, S. et al., 'Colorimetric Effect of Gold Nanocup Arrays on Fluorescence Amplification,' American Chemical Society, J. Phys. Chem 2015, 119, pp. 81518-81526 (10 pages).

* cited by examiner

*Primary Examiner* — Natalia Levkovich
(74) *Attorney, Agent, or Firm* — Thrive IP®; William La Salle, III; Jeremy M. Stipkala

(57) ABSTRACT

The present invention relates to the use of a substrate for enhancing the fluorescence of a fluorescent molecule, wherein the substrate comprises a solid polymer carrier having a plurality of recesses separated from each other and wherein the solid carrier is coated at least in part by a metal.

22 Claims, 15 Drawing Sheets

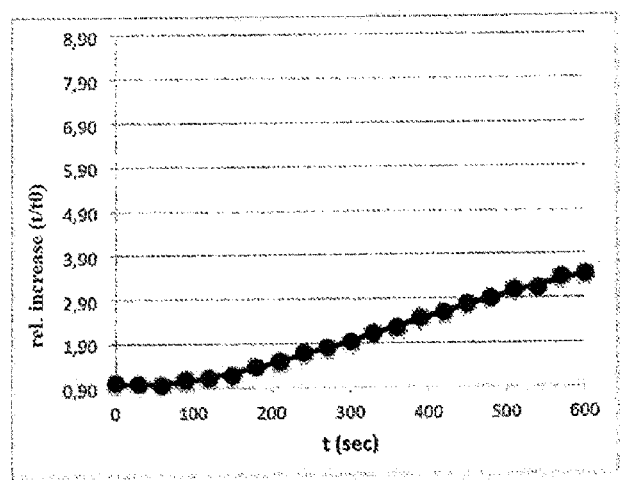
C (550 nm)
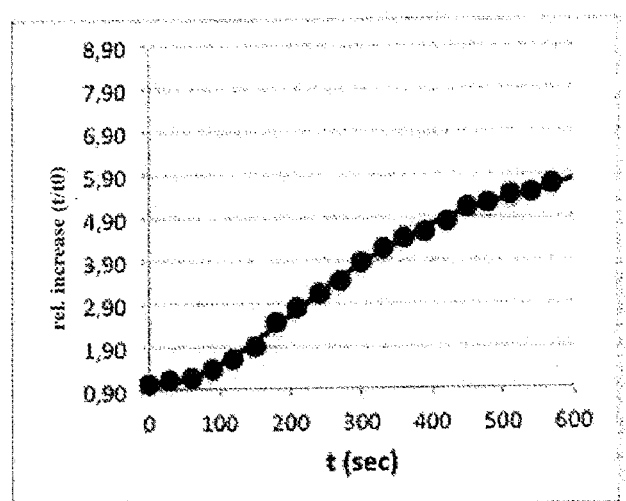
D (755 nm)
Fig. 7 (continuation)

E (874 nm)

Fig. 7 (continuation)

SUBSTRATE FOR FLUORESCENCE AMPLIFICATION

This application represents the U.S. National Phase under 35 U.S.C. § 371 of International Patent Application No. PCT/EP2016/071953, filed on Sep. 16, 2016, and entitled, "SUBSTRATE FOR FLUORESCENCE AMPLIFICATION," which claims benefit of priority under PCT Article 8 to Austrian Patent Application No. A 50793/2015, filed on Sep. 16, 2015, and entitled, "SUBSTRAT ZUR FLUORESZENZVERSTÄRKING;" the disclosures of the foregoing international patent application and Austrian patent application are incorporated herein by reference in their entireties.

The present invention relates to the provision of nano-structured surfaces, which are suited in an especially advantageous manner to enhance the fluorescence of suitable molecules when these molecules approach these surfaces. This effect is also known as metal enhanced fluorescence (MEF) or as surface enhanced fluorescence (SEF).

MEF and SEF are based on an electromagnetic interaction of the incident (exciting), usually coherent (i.e. laser) light with the electron plasma on metal nano-structures. This leads to an enhancement of the light yield of fluorescent molecules when these approach (e.g., bind to) a surface having such metal structures. In this way, molecules bound on the surface will glow more intensively, as their fluorescence is being enhanced.

Due to the enhancement of fluorescence, molecules bound to a surface may be measured at minimal concentrations. For example, the bond of a fluorescence-labelled antibody may be directly traced in the form of the bonding kinetics thereof.

The amount of enhancement is dependent on the shape, size and distance of the metal nano-structures and the type of metal used (e.g., Au, Ag, Al, etc.). In the literature there are found descriptions of spherical (frequently colloids; see, e.g., Yang et al. Small 6(2010): 1038-43; Corrigan T et al J Fluorescence 15 (2005): 777-784), triangular or pyramid-like (see, e.g., Pompa et al. Nature Nanotechnology 1(2006): 126-130; Cade et al. Nanotechnology. 15 (2009): 20 (28)) or wire-like or rod-like metal structures, which are not continuous and form so-called metal islets. The enhancement factors obtained, however, will vary significantly, and the metal nano-structures may not be reproduced in the majority of the cases.

In the US 2005/214841 there are described substrates, which have a plurality of recesses and are coated at least in part by a metal. The substrate may be composed of various materials such as glass, ceramic or metal. Onto the surface of the substrate according to the US 2005/214841, in particular into the recesses thereof, there are applied linkers, which are capable of immobilizing biological substances due to functional groups. In this US application there is not mentioned that the substrates described therein would be suitable to enhance the fluorescence of molecules.

In the U.S. Pat. No. 6,902,705 there are described substrates, which may also comprise recesses and may be coated by a metal (e.g., gold). The surface of the substrates is modified in order to enable the bonding of biological substances (e.g., DNA) onto the surface of the substrate. Providing recesses on the substrate seems to have the advantage that there may be carried out measurements of fluorescence in this way, without receiving any disturbing and interfering signals. Enhancement of the fluorescence signal, however, cannot be achieved using these substrates.

It is an object of the present invention to provide a substrate, which may be produced in a reproducible way and which is able to enhance the fluorescence of a fluorescent substance as soon as the fluorescent substance is brought into the proximity of the substrate (e.g., 10 nm or less), wherein these substrates should allow higher-than-average enhancement factors in MEF measurements.

The present invention relates to a substrate and the use thereof for enhancing the fluorescence of one or several fluorescent molecules, wherein the substrate comprises a solid polymer carrier having a plurality of recesses separated from each other and wherein the solid carrier is coated at least in part by a metal.

It has surprisingly been shown that substrates having the inventive configuration are able to significantly increase the fluorescence yield (quantum yield) of a fluorescent molecule or a fluorophore, respectively, using coherent light or not, if the at least one fluorescent molecule or fluorophore, respectively, is in the proximity (metal-enhanced fluorescence; MEF). "Fluorescence yield" or "quantum yield", respectively, is understood as the ratio between the number of the photons emitted and absorbed.

The fluorescence yield using the substrates according to the invention is even many times higher than the yield using substrates known so far, on the surface of which there are usually situated metallic islets. This increase in the fluorescence yield is surprising insofar as it has been assumed so far that the MEF effect may only occur on surfaces having metallic islets in the form of deposited metal-containing colloids or any other areas on a surface that are isolated from each other and coated by metal (Matveeva E. et al., Anal Biochem 334 (2004): 303-11; Geddes C D., et al. J Fluoresc 12 (2002): 121-129). Substrates having a continuous metal layer or without any elevations, respectively, are known for not exhibiting any or only a very small MEF effect due to a fluorescence quenching effect of the metal surface itself (Pineda E. C., et al. J. Chem. Phys. 83 (1985): 5330-5337; Barnes W. L., J Mod Opt, 45 (1998): 661-699). For this reason, a person skilled in the art without knowledge of the present invention would not have chosen a solid carrier having elevations and a carrier having recesses for coating using a metal.

The substrate according to the invention is used for enhancing the fluorescence of fluorophores. This is, the substrates according to the invention are used wherever there is desired an enhancement of fluorescence (i.e., an increase of the fluorescence yield). For this reason, the substrate according to the invention may be used, e.g., with immunoassays, any form of molecular diagnostics by means of nucleic acids (PCR, RT-PCR), cellular-based bio-assays (as frequently with high-throughput-screening), histological or cellular examinations, multi-plexing test systems (e.g., LUMINEX), provided that fluorescence is used for the detection of the target molecules.

According to a preferred embodiment of the present invention, the enhancement of fluorescence occurred at a distance of 0 to 50 nm, preferably of 1 to 50 nm, even more preferably of 1 to 40 nm, even more preferably of 2 to 40 nm, even more preferably of 1 to 30 nm, even more preferably of 2 to 30 nm, even more preferably of 3 to 30 nm, even more preferably of 1 to 20 nm, even more preferably of 2 to 20 nm, even more preferably of 3 to 20 nm, even more preferably of 5 to 20 nm, even more preferably of 5 to 15 nm, to the metal, which is situated on the surface of the solid polymer carrier.

By "fluorescent molecules", as used herein, there are understood molecules according to the invention, which upon excitation by electromagnetic waves such as, e.g., light at a determined wavelength, will spontaneously emit light.

"Fluorophores" herein is an umbrella term and a synonym for such molecules and comprises thus also molecules, which fluoresce or weakly fluoresce, respectively, and which are usually not designated as fluorophores. Examples of such molecules are proteins and nucleic acids, the fluorescence of which ("intrinsic fluorescence") is mediated via aromatic structures (e.g., via amino acid tryptophan or tyrosine).

The "solid carrier", according to the invention, may also be composed of any polymer material, provided that this may be coated by a metal and recesses may be produced. For example, the solid polymer carrier comprises or is composed of synthetic polymers such as polystyrene, polyvinyl chloride or polycarbonate, cycloolefine, polymethyl methacrylate, polylactate or combinations thereof. In principle, there could also be used non-polymer carriers such as metals, ceramics or also glass, provided that these may be coated by a metal and provided that recesses may be produced.

The solid carrier comprises at least one material selected from the group consisting of thermoplastic polymers and polycondensates.

According to a preferred embodiment of the present invention, the thermoplastic polymer is selected from the group consisting of polyolefins, vinyl polymers, styrene polymers, polyacrylates, polyvinyl carbazol, polyacetal and fluoro-plastics.

The polycondensate is preferably selected from the group consisting of thermoplastic polycondensates, duroplastic polycondensates and polyadducts.

According to an especially preferred embodiment of the present invention, the material of the solid polymer carrier comprises organic and/or inorganic additives and/or fillers, wherein these are preferably selected from the group consisting of $TiO_2$, glass, carbon, colour pigments, lipids and waxes.

A further aspect of the present invention relates to a method for the production of a substrate for enhancing the fluorescence of a fluorophore, comprising the step of coating a solid carrier according to the invention with at least one metal.

Another further aspect of the present invention relates to a substrate for enhancing the fluorescence of a fluorophore, which may be produced according a method according to the present invention.

The solid carriers according to the invention including recesses may in principle be produced using various methods (see FIG. 15).
(a) The solid carriers, including the recesses, are produced in one step (e.g., injection moulding) (see FIG. 15(a)).
(b) The recesses are introduced into an existing solid carrier in further process steps (e.g., hot stamping, electron-beam lithography or extreme ultra violet (EUV) in connection with reactive ion etching or laser ablation) (see FIG. 15(b)).
(c) Onto a solid carrier, there is applied a thin structurable polymer layer, into which the recesses are introduced, such as in the production of BD-50 Blu-ray Disc (UV nano-imprint lithography) (see FIG. 15(c)).

Especially suitable for the production of these structures is the use of the so-called nano-imprint lithography (Chou S. et al., Nano-imprint lithography, Journal of Vacuum Science & Technology B Band 14, No. 6, 1996, S. 4129-4133). For the production of nanostructures by means of nano-imprint lithography, there is required a positive, usually a monomer or a polymer, as well as a nano-structured indenter ("master"). The indenter itself may also be produced by means of nanolithography, wherein this may alternatively also be produced by etching. The positive is applied onto a substrate and subsequently heated above the glass transition temperature, i.e. it is liquefied before the indenter is pressed on. In order to achieve a controllable (and short-term) heating, there is frequently used laser or UV light, respectively. Due to the viscosity of the positive upon heating, the gaps of the indenter are completely filled therewith. Upon cooling, the indenter is then removed. The positive representing the solid carrier of the substrate according to the invention is coated with a metal by means of a sputtering process.

Structuring the indenter for the lithography may again be realized using nano-imprint. As materials, there will be used glass or light-transparent plastic material.

Especially preferred is the production of the solid carrier including recess by means of injection moulding. The mould inserts herein are typically removed from a Si wafer that was lithographically produced by means of Ni galvanics.

The solid carrier may in principle have any shape (e.g., spherical, planar), with a planar shape being especially preferred.

An "recess", as used herein, relates to the level of the surface of the solid carrier that is surrounding the recess, extending into the carrier and, not like an elevation or bump, out of this. An recess in the sense of the present invention has a bottom delimited by the side walls. The depth, hence, is the distance from the surface to the bottom of the recess. The recesses on the solid carrier may have various shapes (e.g., round, oval, quadrangular, rectangular).

A "plurality" of recesses, as used herein, means that the solid carrier according to the invention has at least one, preferably at least two, even more preferably at least 5, even more preferably at least 5, even more preferably at least 10, even more preferably at least 20, even more preferably at least 30, even more preferably at least 50, even more preferably at least 100, even more preferably at least 150, even more preferably at least 200 recesses. These recesses may be provided on a surface of the solid carrier of 1000 $\mu m^2$, preferably of 500 $\mu m^2$, even more preferably of 200 $\mu m^2$, even more preferably of 100 $\mu m^2$. Alternatively, the recesses may extend across a length of preferably 1000 $\mu m$, even more preferably of 500 $\mu m$, even more preferably of 200 $\mu m$, even more preferably of 100 $\mu m$.

"Recesses separated from each other", as used herein, means that the recesses are separated from each other by the lateral limitations thereof and do not have a connection with each other—also not on the surface of the solid carrier.

According to a preferred embodiment of the present invention, the recesses of the solid carrier have a length and a width, wherein the ratio of length to width is 2:1 to 1:2, in particular about 1:1.

The recesses on the solid carrier may in principle have any shape. Especially preferred, however, are recesses, which have a ratio of length to width of 2:1 to 1:2, preferably 1,8:1, preferably 1,6:1, preferably 1,5:1, preferably 1,4:1, preferably 1,3:1, preferably 1,2:1, preferably 1,1:1, preferably 1:1,8, preferably 1:1,6, preferably 1:1,5, preferably 1:1,4, preferably 1:1,3, preferably 1:1,2, preferably 1:1,1, in particular 1:1.

According to a further preferred embodiment of the present invention, the length and the width of the recesses are 0.1 $\mu m$ to 2 $\mu m$, preferably 0.2 $\mu m$ to 2 $\mu m$, preferably 0.3 $\mu m$ to 2 $\mu m$, preferably 0.1 $\mu m$ to 1.8 $\mu m$, preferably 0.2 $\mu m$ to 1.8 $\mu m$, preferably 0.3 $\mu m$ to 1.8 $\mu m$, preferably 0.1 $\mu m$ to 1.5 $\mu m$, preferably 0.2 $\mu m$ to 1.5 $\mu m$, preferably 0.3 $\mu m$ to 1.5 $\mu m$, preferably 0.1 $\mu m$ to 1.2 $\mu m$, preferably 0.2 $\mu m$ to 1.2 $\mu m$, preferably 0.1 $\mu m$ to 1 $\mu m$, preferably 0.2 $\mu m$ to 1 $\mu m$, preferably 0.3 $\mu m$ to 1 µm, preferably 0.1 µm to 0.8 µm, preferably 0.2 µm to 0.8 µm, preferably 0.3 µm to 0.8 µm, preferably 0.1 µm to 0.6 µm, preferably 0.2 µm to 0.6 µm, preferably 0.3 µm to 0.6 µm, most preferably 0.2 µm to 0.6 µm.

Especially preferably, the recesses of the solid carrier according to the invention have an essentially round shape, wherein "essentially round" also includes oval and ellipsoid shapes. The shape of the recess is visible in a top view of the surface of the solid carrier.

The recesses preferably have a depth of 0.1 µm to 5 µm, preferably of 0.1 µm to 4 µm, preferably of 0.1 µm to 3 µm, preferably of 0.1 µm to 2 µm, preferably of 0.1 µm to 1.5 µm, preferably of 0.1 µm to 1.2 µm, preferably of 0.1 µm to 1 µm, preferably of 0.1 µm to 0.9 µm, preferably of 0.1 µm to 0.8 µm, preferably of 0.2 µm to 5 µm, preferably of 0.2 µm to 4 µm, preferably of 0.2 µm to 3 µm, preferably of 0.2 µm to 2 µm, preferably of 0.2 µm to 1.5 µm, preferably of 0.2 µm to 1.2 µm, preferably of 0.2 µm to 1 µm, preferably of 0.2 µm to 0.9 µm, preferably of 0.2 µm to 0.8 µm, preferably of 0.3 µm to 5 µm, preferably of 0.3 µm to 4 µm, preferably of 0.3 µm to 3 µm, preferably of 0.3 µm to 2 µm, preferably of 0.3 µm to 1.5 µm, preferably of 0.3 µm to 1.2 µm, preferably of 0.3 µm to 1 µm, preferably of 0.3 µm to 0.9 µm, preferably of 0.3 µm to 0.8 µm. The depth of the recess is the distance from the surface of the solid metallized carrier to the bottom of the recess.

According to a preferred embodiment of the present invention, the recesses have a distance ("period") to one another of 0.2 µm to 2.5 µm, preferably of 0.3 µm to 1.4 µm, more preferably of 0.4 µm to 1.3 µm. In a further preferred embodiment of the present invention, the recesses have a distance to one another of 0.2 µm to 2 µm, preferably of 0.2 µm to 1.8 µm, preferably of 0.2 µm to 1.6 µm, preferably of 0.2 µm to 1.5 µm, preferably of 0.2 µm to 1.4 µm, preferably of 0.2 µm to 1.3 µm, preferably of 0.3 µm to 2.5 µm, preferably of 0.3 µm to 2 µm, preferably of 0.3 µm to 1.8 µm, preferably of 0.3 µm to 1.6 µm, preferably of 0.3 µm to 1.5 µm, preferably of 0.3 µm to 1.3 µm, preferably of 0.4 µm to 2.5 µm, preferably of 0.4 µm to 2 µm, preferably of 0.4 µm to 1.8 µm, preferably of 0.4 µm to 1.6 µm, preferably of 0.4 µm to 1.5 µm, preferably of 0.4 µm to 1.4, preferably of 0.5 µm to 2.5 µm, preferably of 0.5 µm to 2 µm, preferably of 0.5 µm to 1.8 µm, preferably of 0.5 µm to 1.6 µm, preferably of 0.5 µm to 1.5 µm, preferably of 0.5 µm to 1.4 µm, preferably of 0.5 µm to 1.3 µm, preferably of 0.6 µm to 2.5 µm, preferably of 0.6 µm to 2 µm, preferably of 0.6 µm to 1.8 µm, preferably of 0.6 µm to 1.6 µm, preferably of 0.6 µm to 1.5 µm, preferably of 0.6 µm to 1.4 µm, preferably of 0.6 µm to 1.3 µm, preferably of 0.7 µm to 2.5 µm, preferably of 0.7 µm to 2 µm, preferably of 0.5 µm to 1.8 µm, preferably of 0.7 µm to 1.6 µm, preferably of 0.7 µm to 1.5 µm, preferably of 0.7 µm to 1.4 µm, preferably of 0.7 µm to 1.3 µm, wherein the recesses most preferably have a distance to one another of 0.2 µm to 1.4 µm or 0.3 µm to 1.3 µm, respectively. The distance between the recesses ("period") is measured from the centre of the recess.

According to a further preferred embodiment of the present invention, the metal layer on the solid carrier has a thickness of 10 nm to 200 nm, preferably of 15 nm to 100 nm. Especially preferably the metal layer on the solid carrier has a thickness of 10 nm to 190 nm, preferably of 10 nm to 180 nm, preferably of 10 nm to 170 nm, preferably of 10 nm to 160 nm, preferably of 10 nm to 150 nm, preferably of 10 nm to 140 nm, preferably of 10 nm to 130 nm, preferably of 10 nm to 120 nm, preferably of 10 nm to 110 nm, preferably of 10 nm to 100 nm, preferably of 10 nm to 90 nm, preferably of 10 nm to 80 nm, preferably of 10 nm to 70 nm, preferably of 10 nm to 60 nm, preferably of 10 nm to 50 nm, preferably 15 nm to 200 nm, preferably 15 nm to 190 nm, preferably of 15 nm to 180 nm, preferably of 15 nm to 170 nm, preferably of 15 nm to 160 nm, preferably of 15 nm to 150 nm, preferably of 15 nm to 140 nm, preferably of 15 nm to 130 nm, preferably of 15 nm to 120 nm, preferably of 15 nm to 110 nm, preferably of 15 nm to 90 nm, preferably of 15 nm to 80 nm, preferably of 15 nm to 70 nm, preferably of 15 nm to 60 nm, preferably of 15 nm to 50 nm, preferably 20 nm to 200 nm, preferably 20 nm to 190 nm, preferably of 20 nm to 180 nm, preferably of 20 nm to 170 nm, preferably of 20 nm to 160 nm, preferably of 20 nm to 150 nm, preferably of 20 nm to 140 nm, preferably of 20 nm to 130 nm, preferably of 20 nm to 120 nm, preferably of 20 nm to 110 nm, preferably of 20 nm to 100 nm, preferably of 20 nm to 90 nm, preferably of 20 nm to 80 nm, preferably of 20 nm to 70 nm, preferably of 20 nm to 60 nm, preferably of 20 nm to 50 nm.

According to the invention, the solid polymer carrier is coated "at least in part" by at least one metal. "At least in part", as used herein, means that the solid carrier, in which the recesses are located, is coated by at least one metal at least at 20%, preferably at least at 30%, even more preferably at least at 40%, even more preferably at least at 50%, even more preferably at least at 60%, even more preferably at least at 70%, even more preferably at least at 80%, even more preferably at least at 90%, even more preferably at least at 95%, even more preferably at least at 98%, in particular at 100%, using at least one metal. As the MEF effect implies a metallic surface, it is especially preferred that the surface of the solid carrier is coated by at least one metal at least in the area of the recesses. In this way, the solid carrier may comprises also several (e.g., at least two, at least three, at least four or at least five) metal layers that are arranged one on top of the other and comprise different metals. An advantage of the use of several layers of metal on the solid carrier is that the first metal layer (e.g., chromium), which is applied directly onto the carrier, may improve adherence of the further metal layers.

The term "arranged one on top of the other", as used herein, means that a metal layer is arranged indirectly or directly on another metal layer. In this way, there is formed a multi-layered system of metal layers of the same metal or of different metals.

The metal layers are preferably continuous and not-intermittent. According to the invention, however, it was possible to find that the metal layer or metal layers on the solid polymer carrier may also be intermittent, without the fluorescence enhancing effect being impaired thereby. The intermittent metal layer, for example, may be realized by a conductivity measurement of the surface of the substrate according to the invention. A lower or no conductivity, respectively, means that the metal layer(s) on the substrate surface are intermittent. Intermittent metal layers may, for example, be produced by a substrate that is essentially completely coated by a metal being contacted with a preferably salt containing solution, such as, e.g., 10 mM phosphate buffer with 150 mM NaCl, for a determined period of time (10-90 minutes).

The solid carrier of the present invention is "coated at least by one metal". Preferably, the metal layer comprises at least two, more preferably at least three, more preferably at least four, more preferably at least five different metals. The metals may be applied onto the solid carrier by means of methods known in prior art, wherein there is preferably made use of sputtering (cathode sputtering) or thermal evaporation, electron-beam physical vapour deposition, pulsed laser deposition, cathodic arc deposition, molecular beam epitaxy, ionic beam supported deposition and ion plating.

According to a preferred embodiment of the present invention, the metal is selected from the group consisting of silver, gold, aluminium, chromium, indium, nickel, palladium, platinum, zinc, tin and alloys comprising one or several of these metals.

According to the invention, these metals or alloys, respectively, may be used for coating the solid carrier according to the invention. Especially preferred is coating of the solid carrier using silver or alloys comprising silver, as silver or the alloys thereof, respectively, show an especially high enhancement effect. Especially preferred is an alloy, which comprises silver, indium and tin. The silver-containing alloys preferably have a silver content of more than 10%, more preferably more than 30%, even more preferably more than 50%, even more preferably more than 70%, even more preferably more than 80%, even more preferably more than 90%.

After coating of the solid carrier with at least one metal or before using the substrate according to the invention or the solid carrier according to the invention, respectively, the solid carrier or the substrate, respectively, are treated with an aqueous composition comprising at least an acid or a salt of a halogen selected from the group consisting of fluorine, chlorine, bromine and iodine.

It has been shown that fluorescence enhancement through the pre-treatment of the substrate or the solid carrier, respectively, with an aqueous solution (e.g., a buffer) comprising at least an acid of a halogen or a salt thereof may even be further enhanced. For this reason, it is especially preferred to pre-treat the solid carrier or the substrate, respectively, with an acid- or salt-containing solution.

Alternatively, the aqueous solution (e.g. a buffer) comprising at least an acid or a salt of a halogen may be used instead of other solutions also during measurement.

According to the invention, all acids of the halogen group or the salts thereof are suitable, with the radioactive halogens, however, not being desired in practice. There are especially preferably used the acids or salts of the halogens fluorine, chlorine, bromine and iodine, with chloride being most preferred, in particular metal chlorides. The acids or salts that are used according to the invention are especially preferably alkali metal salts or alkaline earth metal salts, in particular sodium, potassium or lithium salts.

According to an especially preferred embodiment of the present invention, the aqueous composition comprises at least an acid or a salt selected from the group consisting of HCl, HF, HBr, HJ, NaCl, NaF, NaBr, NaJ, KCl, KF, KBr and KJ.

The aqueous composition comprising at least an acid of a halogen or a salt thereof may in addition to the at least one acid or the salt thereof further comprise further substances such as, e.g., other acids or salts. Especially preferably there are used substances having a buffering function (e.g., disodium hydrogen phosphate, potassium dehydrogenate phosphate, carbonate).

According to a further preferred embodiment of the present invention, the solid carrier is treated with the aqueous composition for at least 1, preferably at least 2, more preferably at least 5, even more preferably at least 10, even more preferably at least 20 minutes.

According to the invention it has been shown that the fluorescence enhancing effect of the carrier coated by at least one metal is especially high if the solid carrier is incubated for at least 1 minute with the aqueous composition comprising at least an acid of a halogen or a salt thereof, preferably at room temperature (22° C.). If the incubation is carried out at higher temperatures (e.g., between 30° C. and 40° C.), then the incubation period may be reduced correspondingly (e.g., at least 30 seconds). If the incubation is carried out, however, at lower temperatures (e.g., between 10° C. and 20° C.), then the incubation period may be prolonged correspondingly (e.g., at least 2 minutes).

According to a preferred embodiment, the substrate according to the invention is part of a capillary tube, a microtiter plate, a microfluidic chip, an assay strip (for lateral flow assays), of a carrier (e.g., slide carrier) for fluorescence microscopy, in particular for high-resolution methods such as confocal laser microscopy according to the point scanner principle as well as 4Pi microscopes and STED (stimulated emission depletion) microscopes, a sensor array or another optical detector field.

Especially preferably is the use of the substrate according to the invention in microtiter plates, wherein the microtiter plates may comprise 6, 12, 24, 48, 96, 384 or 1536 wells. Microtiter plates are used for various measurements and assays, in which there is frequently measured the fluorescence of samples. By provision of the substrate according to the invention in the wells of microtiter plates, the fluorescence yield of the samples may be significantly increased. The substrates may be introduced into and fixed in the wells by means of various methods. The substrates may be fixed therein by means of glue, welding techniques (e.g., laser welding) and thermal joining in the wells.

According to an especially preferred embodiment of the present invention, the solid carrier comprises or is composed of a cycloolefine co-polymer or cycloolefine polymer and it is part of a microtiter plate or part of the wells of a microtiter plate, respectively. In this regard, COP 1060R (Zeonor® 1060R) has proven to be especially suitable. The carrier is therein coated by preferably 10 to 60 nm, preferably up to 40 nm, metal (e.g., silver).

Certain measurements using fluorescent substances such as fluorophores are carried out in capillary tubes. For this reason, it is preferred to provide the substrates according to the invention in capillary tubes. An exemplary use therefor is the cytometry or flow cytometry, respectively, wherein the number and also the type of fluorescent cells or fluorescence-labelled cells is determined using a fluorescence measurement.

Numerous applications for the measurement of fluorescence are carried out in microfluidic chips (e.g., as "lab-on-a-chip" application), wherein the substrates according to the invention may be provided in the detection line of such chips.

The substrates according to the invention may also be provided in conventional cuvettes. In this way, the fluorescence yield may also be significantly increased in fluorescence measurements so that even the smallest amounts of fluorescent substances in a sample may be measured. Any cuvette form may be used according to the invention.

The substrates according to the invention (e.g., in the "detection line") may also be used with assay strip systems (lateral flow assays), which are used for rapid-tests or in-field-tests (point of care), in order to enhance the fluorescence of a labelled analyte (e.g., a fluorescence-labelled antibody) and, in this way, improve the sensitivity of the tests.

In a further preferred embodiment of the invention, the substrates according to the invention are applied onto slide carriers as used in microscopy, in particular fluorescence microscopy. The fluorescence of fluorophores used for labelling cellular structures may thus be selectively enhanced, and the optical resolution of the methods may be drastically improved, as there is required less intensity of light, which would optimize the ratio signal/noise. Areas of application would be high-resolution methods such as confocal laser microscopy according to the point scanner principle as well as 4Pi microscopes and STED (stimulated emission depletion) microscopes.

According to a further preferred embodiment of the present invention, the metal coating on the surface of the substrate comprises at least in part molecules for the direct and/or indirect bonding of fluorescent molecules.

The substrates according to the invention may enhance the fluorescence of fluorescent molecules or fluorophores, respectively, if the fluorophores are positioned in a spatial proximity (preferably less than 20 nm) of the substrates. The fluorophores or the fluorescent substances, respectively, may then move freely in a liquid, wherein the fluorescence increase is only realized if these fluorophores or fluorescent molecules, respectively, approach the substrate according to the invention. In order to increase the probability of the approach of the fluorophores or the fluorescent molecules, respectively, towards the substrate, it is especially advantageous if molecules are irreversibly or reversibly bound to the surface of the substrate (i.e. on the metal coating), which may bind either the fluorophore or the fluorescent molecule itself ("direct bonding"), respectively, or a molecule, to which a fluorophore or a fluorescent molecule is coupled (e.g., fluorescence-labelled antibody; "indirect bonding"). Methods for bonding such molecules to metal structures are adequately known. In the simplest case, a bond is realized via physical-chemical adsorption (mediated via ionic and hydrophobic interaction) of the proteins onto the metal surface (e.g., Nakanishi K. et al. J Biosci Bioengin 91 (2001): 233-244). There are also known covalent methods for immobilizing proteins following the derivatization of the metal surfaces (e.g., GB Sigal et al. Anal Chem 68 (1996): 490-7).

Molecules for the direct and/or indirect bonding of fluorescent molecules or of fluorophores, respectively, are preferably selected from the group consisting of antibodies, antibody fragments, preferably Fab, F (ab) '2 or scFv fragments, nucleic acids, enzymes, lipids, virus particles, aptamers and combinations thereof.

On the one hand side, these molecules are able to directly bind fluorophores or fluorescent molecules (e.g., antibodies and fragments thereof, nucleic acids, enzymes), on the other side, these molecules may also bind other molecules, which are provided with a fluorophore or a fluorescent substance, respectively.

A further aspect of the present invention relates to a capillary tube, a chip, preferably a microfluidic chip, a cuvette, a microtiter plate, a carrier for fluorescence microscopy or an optical detector field comprising a substrate according to the invention.

Still a further aspect of the present invention relates to a set comprising at least one microtiter plate, at least one capillary tube, at least one chip, preferably a microfluidic chip, at least one cuvette and/or at least one assay stripe comprising a substrate according to the invention and an enzyme-labelled and analyte-binding molecule and a fluorescence substrate for the enzyme.

"Fluorescence substrate for an enzyme", as used herein, is a substrate, which is able to bind in or on an active centre of the enzyme, whereby the substrate may obtain fluorescent properties. Naturally, the substrate may also have fluorescent properties already before attachment to the enzyme.

The solid carriers having the recesses as defined above are subsequently coated with one or several metals (e.g., two, three, four or five metals). Methods for coating solid carriers with metals are well-known among those skilled in the art, wherein there are preferably used PVD methods (physical vapour deposition) such as sputtering methods and vacuum evaporation methods.

For this reason, according to a preferred embodiment of the present invention, the at least one metal is applied onto the surface of the solid carrier by means of a sputtering process or thermal evaporation, electron-beam physical vapour deposition, pulsed laser deposition, cathodic arc deposition, molecular beam epitaxy, ionic beam supported deposition or ion plating or any other process according to the respective prior art.

In order to enable the direct and/or indirect bonding of fluorophores or any other fluorescent substances onto the surface of the substrate according to the invention, molecules are applied on the metal coating on the surface of the substrate at least in part in order to enable the direct and/or indirect bonding of fluorophores via adsorptives or via covalent chemical derivatization.

"At least in part", as used herein, means that at least 10%, preferably at least 30%, more preferably at least 50%, more preferably at least 70%, more preferably at least 80%, more preferably at least 90%, in particular 100%, of the solid carrier coated by a metal are provided with molecules for the direct and/or indirect bonding of fluorophores.

According to a preferred embodiment of the present invention, the molecules for the direct and/or indirect bonding of fluorophores are selected from the group consisting of antibodies, antibody fragments, preferably Fab, F (ab) '2 or scFv fragments, nucleic acids, enzymes, lipids, virus particles, aptamers and combinations thereof.

A further aspect of the present invention relates to a method for determining or for quantifying at least one analyte in a sample, comprising the steps of:

a) optional direct or indirect labelling of at least one analyte with at least one fluorophore, b) applying at least one labelled analyte from step a) or a fluorescent analyte onto a substrate according to the present invention, c) exciting at least one fluorophore by irradiation of the substrate using light at an appropriate wavelength, and d) measuring the fluorescence in order to determine the presence of at least one analyte in the sample.

The substrate according to the invention, which is able to significantly increase the fluorescence yield of fluorophores and any other fluorescent molecules or substances, may be used for methods, wherein the fluorescence of samples is to be measured. By using the substrate according to the invention in such methods, it is possible to significantly increase the sensitivity of such methods such that not only the presence of smallest amounts of analytes to be determined may be determined but rather also the quantification (of small amounts) of analytes may be performed more exactly.

In a first step, the analytes in a sample that are to be determined or quantified, respectively, are directly or indirectly labelled using a fluorophore or a fluorescent substance. In a direct labelling of the analyte, the at least one fluorophore or the at least one fluorescent substance is bound covalently or non-covalently (e.g., by means of hydrogen bridging, electrostatic bonding, Van-der-Waals forces, hydrophobic interactions) to the analyte to be determined or quantified, respectively. In an indirect labelling, fluorescence labelled molecules (e.g., antibodies or fragments thereof), which are able to bind to the analyte, are introduced into the sample. This first process step is optional, as there are analytes to be determined or quantified, respectively, which themselves are already able to fluoresce upon appropriate excitation. Samples comprising such analytes may be applied onto the substrate according to the invention directly or upon sample processing (see step b) of the method according to the invention).

Upon applying the at least one labelled analyte from step a) or the fluorescent analyte onto the substrate according to the invention, the fluorophore or the fluorescent substance or the fluorescent analyte, respectively, is excited by means of irradiation using coherent or non-coherent light (e.g., laser or xenon flash light) at an suitable wavelength for fluorescence emission.

"Light at a suitable wavelength", as used herein, means that the light used in the method according to the invention has a wavelength that is suited to induce the fluorescence emission of a substance upon contact. For example, light having a wavelength of 485 nm is suitable to induce the fluorescence emission of fluorescein isothiocyanate (FITC).

Upon excitation of the fluorescent substances by means of light, these substances will emit light (fluorescence) at a determined wavelength. This emitted light having a defined wavelength is measured and may be used in order to quantify or determine the presence of an analyte in a sample. The emitted light may be measured using a detector (e.g., photo multiplier). Herein, there may be used commercially available microtiter plate readers (Tecan F200pro, BioTek Synergy, Molecular Devices FilterMax or SpectraMax series, etc.), Flat Bed Fluorescence Scanner (e.g., Tecan LS-Reloaded, fluorescence microscopy or any other proprietary analysis system (Roche COBAS, Abbot AxSYM, Behring Opus Plus), if an appropriate fluorescence detector is integrated).

According to a preferred embodiment of the present invention, the at least one fluorophore has an emission wavelength in the range of 360 to 780 nm, preferably of 490 to 680 nm.

According to a further preferred embodiment of the present invention, the at least one fluorophore has an emission wavelength in the range of 410 to 800 nm, preferably of 510 to 710 nm The at least one fluorophore is preferably selected from the group consisting of methoxy coumarine, amino coumarine, Cy2, Alexa Fluor 488, fluorescein isothiocyanate (FITC), Alexa Fluor 430, Alexa Fluor 532, Cy3, Alexa Fluor 555, 5-TAMRA, Alexa Fluor 546, phycoerythrine (PE), tetramethyl rhodamine isothiocyanate (TRITC), Cy3.5, rhodamine, Alexa Fluor 568, Alexa Fluor 594, Alexa Fluor 633, Alexa Fluor 647, Cy5, Alexa Fluor 660, Cy5.5, Alexa Fluor 680 and Cy7, preferably from the group consisting of fluorescein isothiocyanate (FITC), Cy3, phycoerythrine (PE), tetramethyl rhodamine isothiocyanate (TRITC), Cy5 and Alexa Fluor 680.

According to a preferred embodiment of the present invention, the indirect labelling of the analyte with at least one fluorophore is realized via a fluorophore-labelled and analyte-binding molecule.

According to a further preferred embodiment of the present invention, the analyte-binding molecule is selected from the group consisting of antibodies, antibody fragments, preferably Fab, F (ab) '2 or scFv fragments, nucleic acids, enzymes, lipids, virus particles, aptamers and combinations thereof.

The present invention is explained in greater detail by way of the following figures and examples, without, however, being limited thereto.

FIG. 1 shows a three-dimensional AFM (atomic force microscope) illustration of a planar solid carrier according to the invention that is coated by a metal (see example 1).

FIG. 2 shows the MEF effect in dependence on the type of fluorophore and a silver layer thickness of 0, 20 and 50 nm Ag. The MEF effect is visible in the "relative increase" that is observed, this is the ratio of the signal at the end of the measurement period after 600 seconds (t600) to the signal at the beginning of the measurement t(0). A relative increase of 1.0 means no change of signal and, hence, no MEF. The higher the relative increase, the stronger is the MEF effect. There is observed a general trend towards stronger MEF with increasing metal layer thickness, which, however, will vary from fluorophore to fluorophore.

Figure 12:
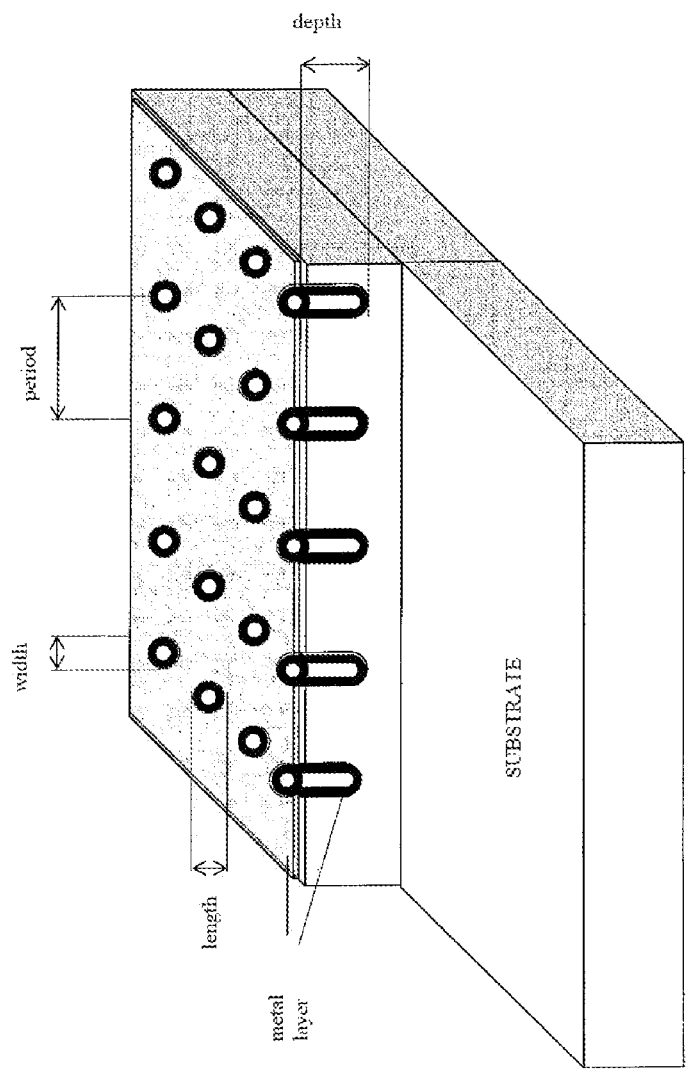

FIG. 12 shows the substrate according to the invention comprising a carrier that is coated by a metal layer. The solid carrier has recesses having a depth, a width and a length. The recesses are located on the solid carrier at a determined distance (period) to one another.

Figure 13:
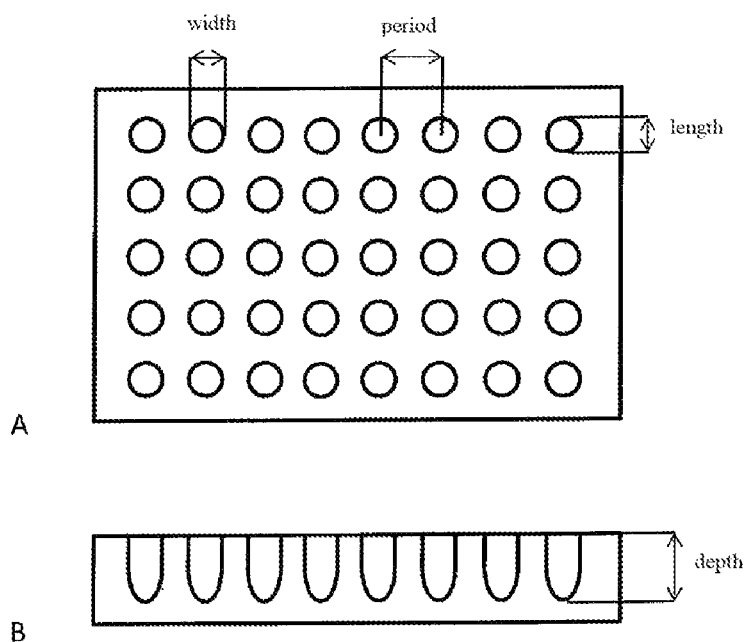

FIG. 13 shows the top view (A) and a sectional view (B) of a solid carrier according to the invention. The recesses on the solid carrier are characterized by a width, a length and a depth and have a determined distance (period) to one another.

Figure 14:
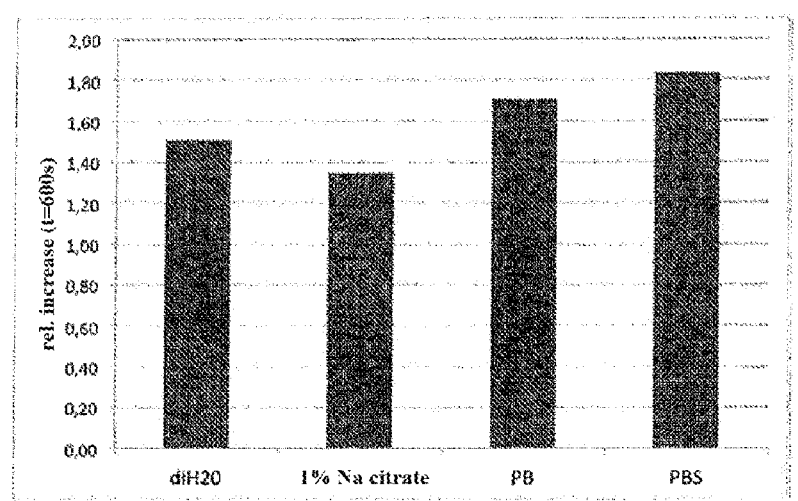

FIG. 14 shows the MEF effect upon use of various buffers.

Figure 15:
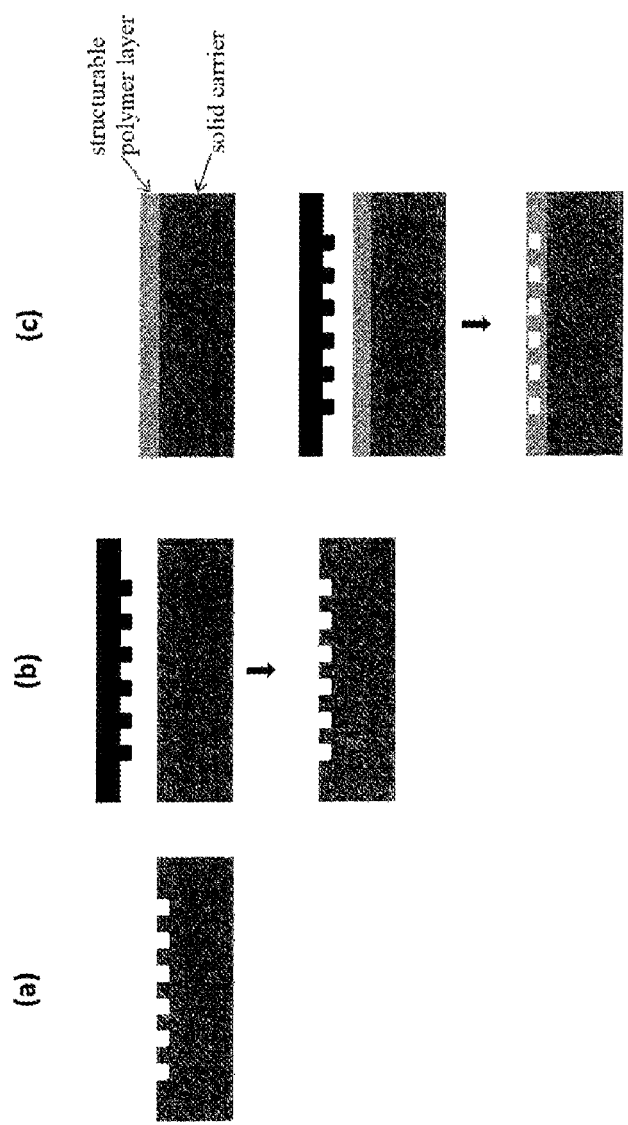

FIG. 15 shows various methods by means of which the solid carriers according to the invention, including recesses, may be produced.

EXAMPLES

Example 1

Production of the Substrate According to the Invention

Based on prior art that is known (see, among others, Pompa et al. Nature Nanotechnology 1 (2006): 126-130; Cade et al. Nanotechnology. 15 (2009): 20 (28), US 2009/0262640), there has been attempted to produce as high and slender tower- or pillar-like structures ("nano pillars") as possible in order to achieve, due to an as high ratio (1:2 to 1:3) of the diameter of the base to the height of the structure ("aspect ratio") as possible, a thinning of the metal layer upon evaporation and, hence, the production of the metal islet structures required for the MEF effect according to the literature. For this reason, there were produced "pillars"

(elevations) having different base diameters (250-550 nm) and different heights (250-850 nm).

For the production of the substrates, there was used a special form of injection moulding, namely injection embossing. In injection embossing, a thermoplastic plastic melt is introduced into a slightly opened tool with a pressing process (=embossing) being simultaneously carried out. The nano-structured indenter for the injection moulding was removed from a lithographically produced silicon master by means of nickel galvanics. Silicon master means herein a silicon wafer coated by a positive lacquer, which has been exposed and subsequently developed by means of "laser lithography".

Figure 10:
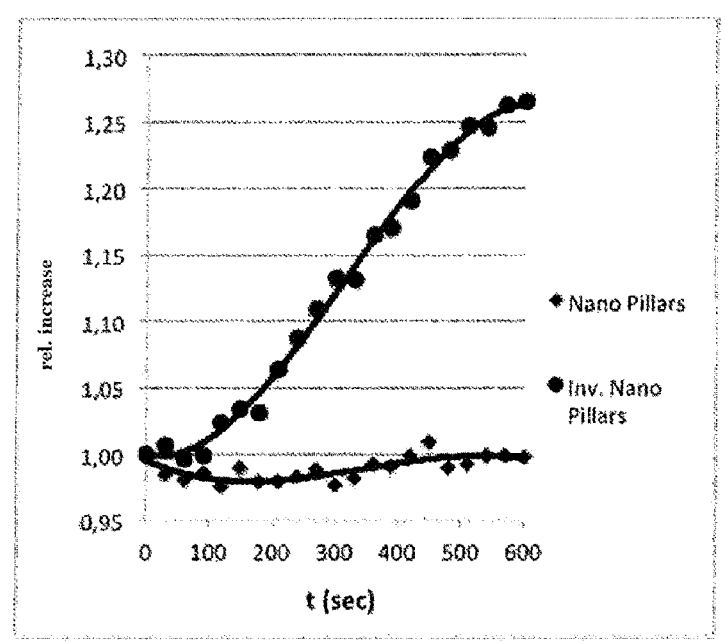
FIG. 10 shows a MEF kinetics on nano-pillars (elevations) and inverted nano-pillars (recesses).

Surprisingly, only the solid carriers coated by metal and having recesses (INPs) show a marked MEF effect, whereas the substrates based on a solid carrier having elevations showed no or only a minimal MEF effect (see FIG. 10). For this reason, the INP structures were further investigated.

Example 2

Influence of the Metal Layer Thickness

In order to investigate the influence of the metal layer thickness on the surface of a solid carrier having recesses with a diameter of about 450 µm, various layer thicknesses of silver were vacuum deposited.

The direct adsorption of fluorescence-labelled antibodies on a surface is the easiest way in order to compare differently structured surfaces in regard to sensitivity and enhancement factor. The MEF effect was thereby shown in that, in contrast to a surface without MEF, the bonding kinetics ("MEF kinetics") of the antibody could be examined in real-time. This was possible as the molecules in the proximity of the surface will glow more, however, the un-bound molecules farther away will not. The solution with the fluorescence-labelled antibody was then placed dropwise onto the corresponding nano-structured surface, and the change of the signal over time was tracked using a suitable fluorescence measurement device (Tecan 200F pro).

Apart from the parameter "MEF kinetics", it is possible to define an enhancement factor due to the comparison of a signal of a certain concentration of a fluorescence-labelled antibody on a surface having a nano-metal structure with a signal of the same antibody on a surface without this structure. It is merely to be ensured that the effective occupation densities, this is the actual amount of antibodies on the surfaces, are the same.

This may easily be performed by detecting the bound antibody (goat anti-rabbit FITC) using a labelled secondary antibody (a donkey anti-goat antibody labelled with alkaline phosphatase), exhibiting no significant differences in the antibody occupation densities of the surfaces tested.

Figure 1:
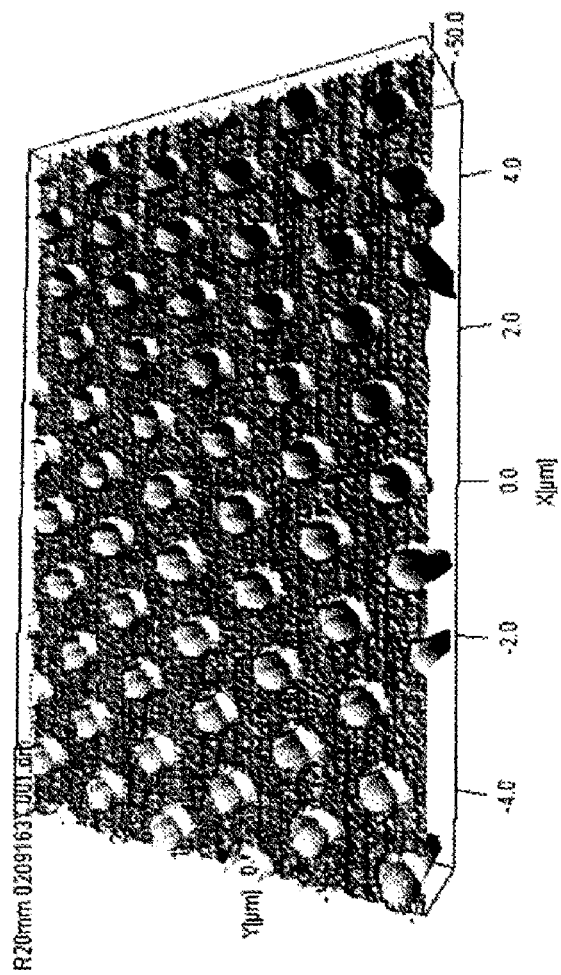
Figure 2:
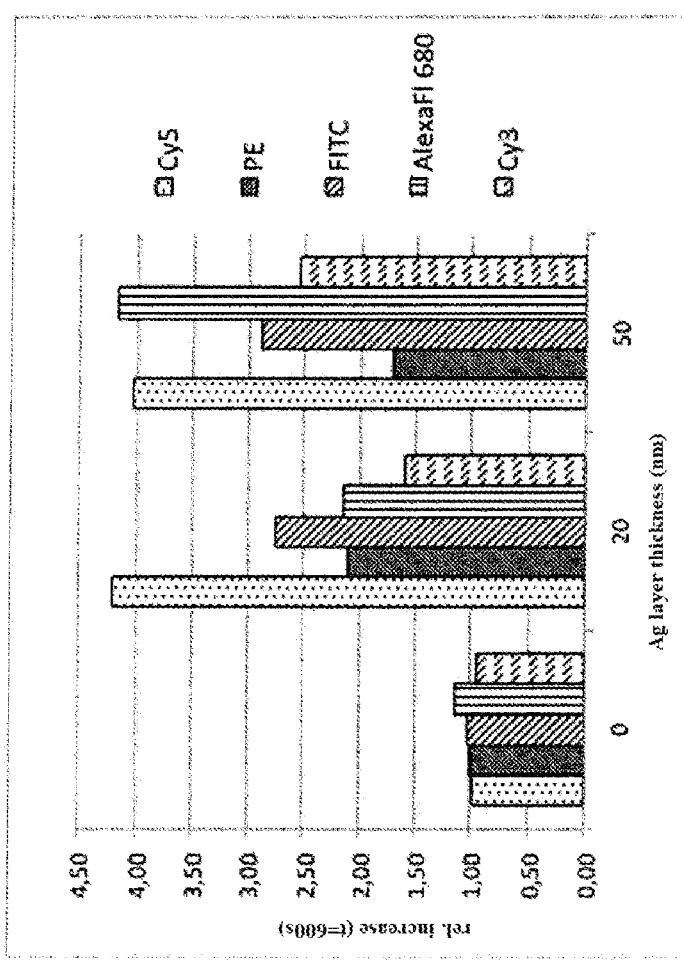

In the case of the metal layer thickness variants produced it was then shown that the MEF effect in the area of 0-50 nm Ag increases significantly, independently of the fluorophore tested (see FIG. 2; relative increase of 1 means no MEF effect).

Figure 3:
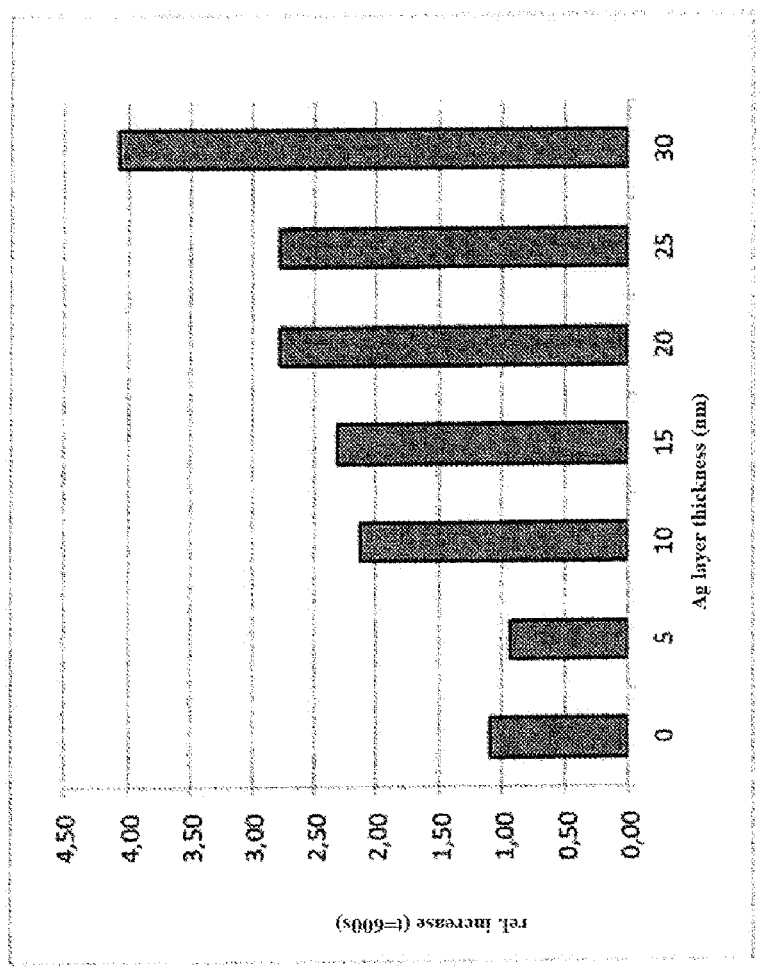
FIG. 3 shows the dependence of the MEF on the silver layer thickness in 5 nm increments for AlexaFlour 680 (see example 2). Starting at a layer thickness of 5 nm, there is to be observed a marked increase of the MEF effect.

FIG. 3 shows that a minimum layer thickness of 5 nm is required in order to obtain an MEF. FIG. 3 further shows that in the case of an increase of the metal layer thickness in 5 nm increments, there will be observed a continuous increase of the MEF effect.

Example 3

Influence of the Structure Period

The distance of the recesses to one another ("period") could exert an influence on the MEF effect of the substrate according to the invention. For this reason, various solid carriers having different periods were, for example, coated with silver:

| Field | Period (µm) |
|---|---|
| 1 | 0.8 |
| 2 | 1.0 |
| 3 | 1.4 |
| 4 | 1.6 |
| 5 | 1.8 |
| 6 | 2.0 |
| 7 | 2.2 |

Figure 4:
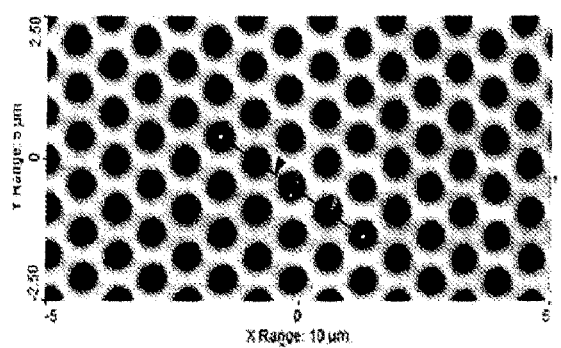
FIGS. 4 and 5 show AFM pictures of substrates/structures according to the invention, including recesses having a different period.
Figure 5:
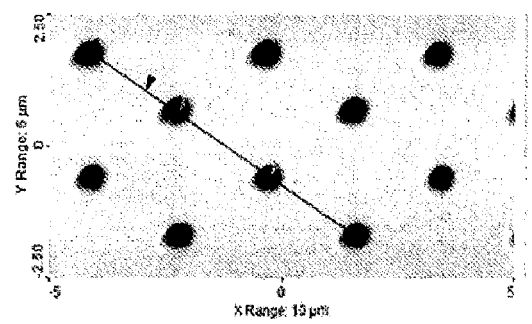

The FIGS. 4 and 5 respectively show an AFM picture of two substrates according to the invention having a period of 0.8 µm or 2.2 µm, respectively, and a silver layer thickness of 50 nm.

Figure 6:
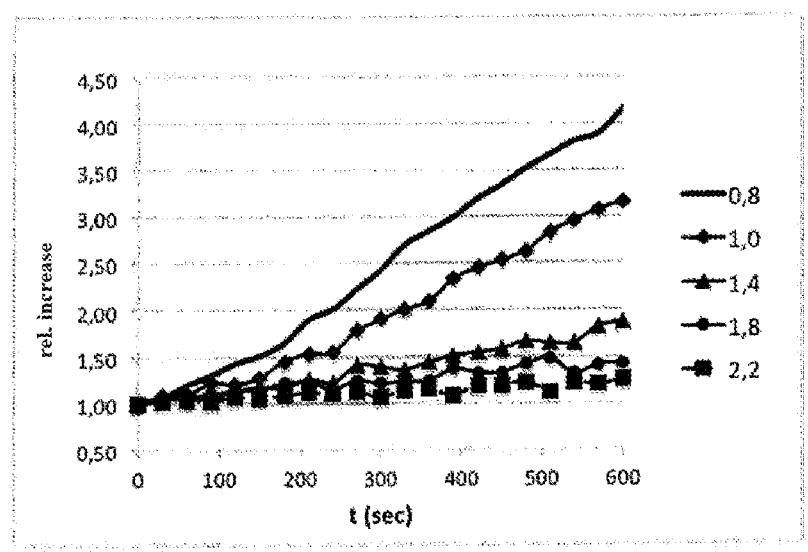
FIG. 6 shows the dependence of the MEF effect on the period (0.8 to 2.2 μm) of the structures.

In order to find proof for the MEF effect, for all fields 1 to 7 there were produced MEF kinetics of AlexaFlour 680 (13 nM in 10 mM PBS, pH 7.4) (see FIG. 6). In this regard, it was possible to determine that with a period of 0.8 and 1.0 µm, the MEF effect was the highest. Starting at a period of 1.2 nm, the MEF effect was markedly lower, but still present.

The following table indicates the relative increases (signal t=300s/signal t=0s) of the measurements of the MEF kinetics of various fluorescence-labelled antibodies for field 1 (0.8 um) and 2 (1.0). The silver layer thickness on the INPs for these measurements was 20 nm, wherein there was used a goat anti-rabbit IgG antibody (diluted in 10 mM PBS pH 7.4; c=13 nM) labelled with the respective fluorophore:

|  | Field 1 | Field 2 |
|---|---|---|
| FITC | 1.6 | 1.6 |
| Cy5 | 1.9 | 2.1 |
| TRITC | 1.8 | 1.8 |
| PE | 1.3 | 1.3 |
| Cy3 | 2.3 | 3.2 |
| AlexaFl680 | 1.7 | 1.7 |

The MEF effect on the INPs, thus, could be demonstrated for various fluorophores in the wavelength range Ex/Em of 485/520 (FITC) to 680/720 (AlexaFlour 680). The use of the INPs is not limited to special fluorophores.

Example 4

Influence of the Depth of the Recesses on the MEF Effect

In order to investigate the influence of the depth of the recesses (inverted nano-pillars; INPs), there were produced solid carriers having different recess depths (60 nm, 240 nm, 550 nm, 755 nm and 874 nm) and vacuum deposited using silver (20 nm layer thickness).

Figure 7:
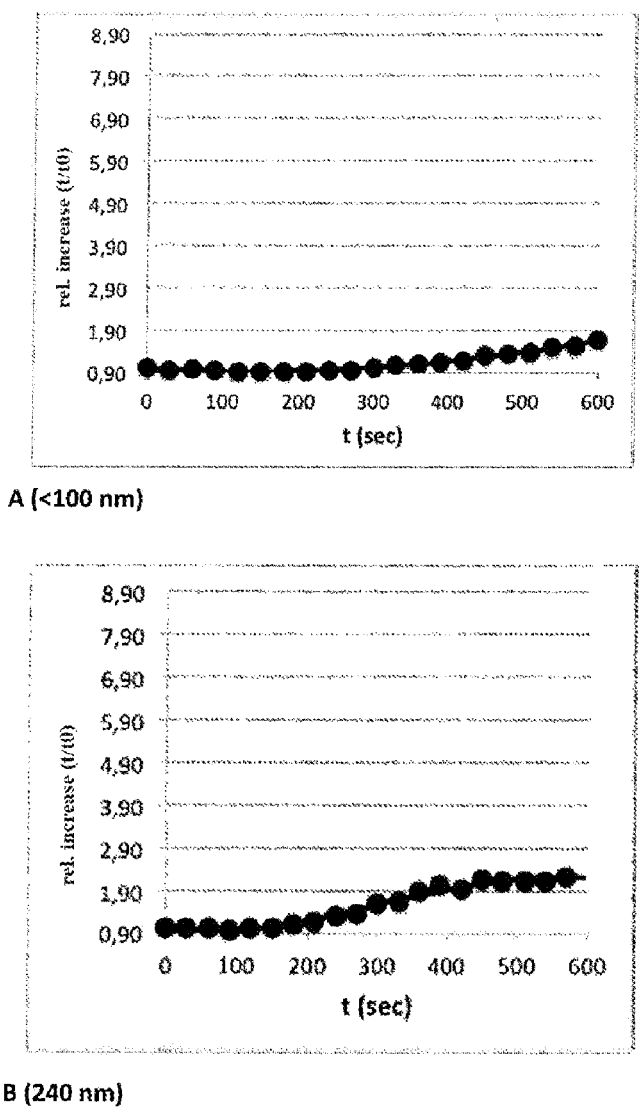
FIG. 7 shows the dependence of the MEF on the depth of the structures.
Figure 8:
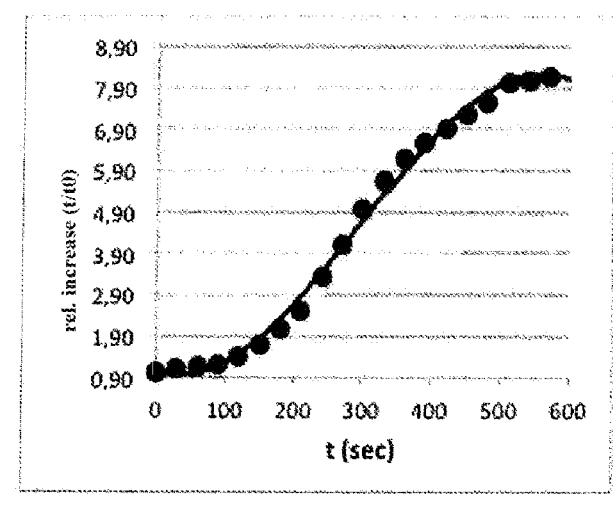
FIGS. 8 and 9 show the MEF enhancement factors obtained compared to surfaces coated by colloid and MEF surfaces from prior art (company PLASMONIX; QuantaWells 2; "competitor structure").
Figure 8:
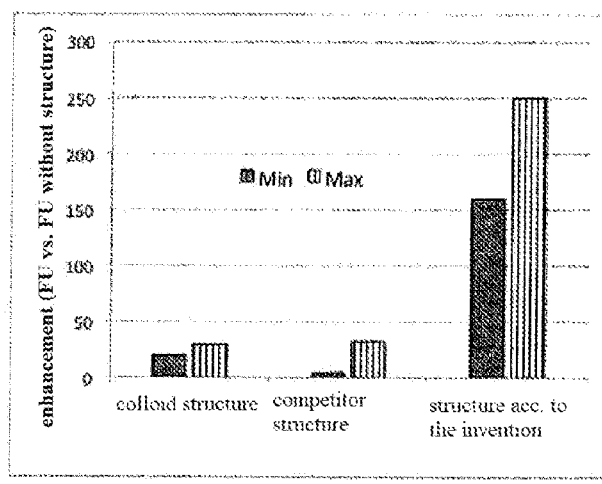

Adsorption tests with fluorescence-labelled antibodies ("MEF kinetics") showed that the MEF effect will increase with increasing recess depth. With solid carriers having recesses of less than 60 nm in depth, however, there was determined a MEF effect, this being, however, significantly lower in comparison to the other carriers (see FIG. 7).

Example 5

Comparison Trials

The substrates according to the invention, in comparison to commonly used structures, showed an enhanced MEF effect. In order to find proof thereof, microtiter plates were coated according to a method known from the literature (Direct monitoring of molecular recognition processes using fluorescence enhancement at colloid-coated microplates, C Lobmaier et al July 2001; 14(4): 215-22) with silver colloids, and the enhancement factors thereof (defined as the ratio of the signals on the surface without and with silver colloids at the same antibody surface concentration) were estimated compared to the structures according to the invention having recesses (20 nm Ag, 0.8 μm period). In addition, the only commercial microtiter plate system based on MEF according to the manufacturer information (company PLASMONIX; Quant-Wells 2) was investigated.

Figure 9:
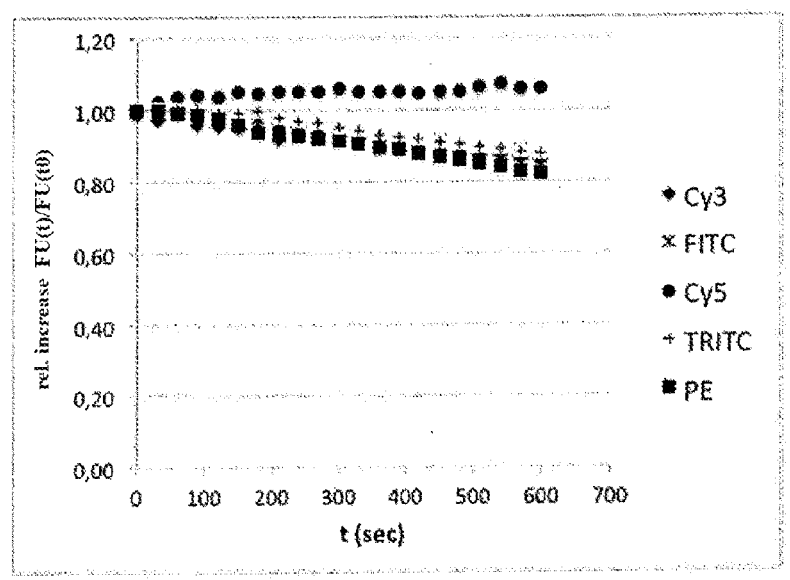

The enhancement factors of the substrate according to the invention were, as shown in FIG. 9, 10 times higher than on colloid plates or on plates by PLASMONIX. Apart from the markedly lower enhancement factors, the microtiter plates by PLASMOX further do not show the typical MEF kinetics (see FIG. 9 in comparison to FIG. 7).

Example 6

Anti-Rabbit IgG Fluorescence Immunoassay

Figure 11:
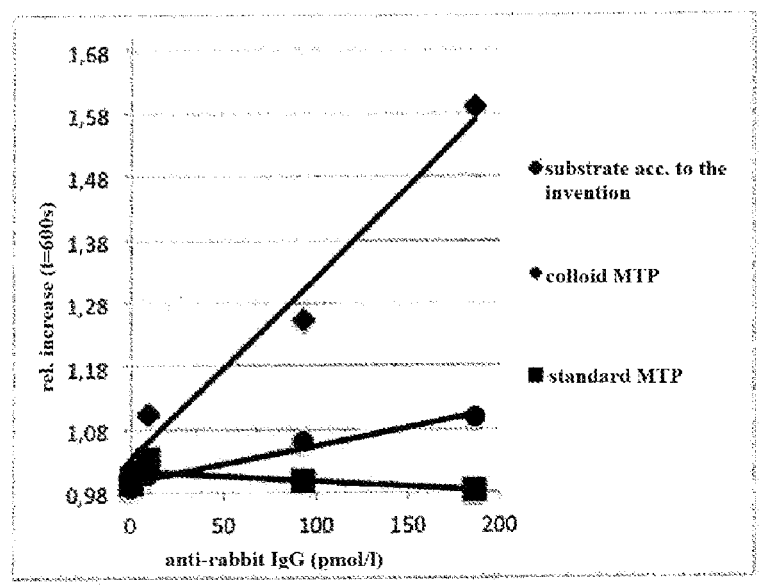
FIG. 11 shows an anti-rabbit IgG fluorescence immunoassay using a substrate according to the invention being performed.

The surfaces of a substrate according to the invention, of a colloid-coated microtiter plate (MTP) and a standard microtiter plate by the company Greiner, as used for immunoassays according to prior art, were contacted with a solution of rabbit IgG (2 μg/ml) in PBS (10 mM phosphate buffer with 150 mM NaCl pH 7.4) for 2 h at room temperature. Then the solution was removed, the surface with PBS containing 0.11% Triton X-100 was washed and contacted for 1 h with a 5% polyvinyl pyrolidone solution for blocking any unspecific bonds. Following a further washing step using PBS/Triton X100, there was carried out an incubation with biotin-labelled anti-rabbit IgG antibodies of various concentrations for 1 h at r.t. Bonding of this anti-rabbit IgG antibody was finally, after a final washing step, detected by means of a MEF kinetics measurement using Cy3-labelled streptavidin over a period of 600 seconds (see FIG. 11). It is clearly visible that there did not occur any MEF kinetics on the standard microtiter plate, hence, the immunoassay also not being performable. The colloid-coated microtiter plate, however, shows only a slight MEF kinetics, with the substrate according to the invention, however, showing a markedly distinctive MEF kinetics and thus also an immunoassay having an essentially steeper calibration curve, this is, significantly higher sensitivity.

The substrate according to the invention used in this example showed electric conductivity before the coating thereof with antibodies. Upon measurement of MEF kinetics, no electric conductivity of the substrate could be detected. This could also be caused by the formation of silver chloride upon contact with PBS buffer.

Example 7

MEF Effect in Dependence on the Buffer Used

In order to investigate the dependence of the MEF effect on the buffer used, the MEF kinetics due to the adsorption of a fluorescence-labelled antibody (goat anti-rabbit antibody, labelled with Cy5) was observed, as in example 3, wherein instead of the PBS buffer there was used a pure phosphate buffer (PB; 10 mM phosphate buffer), 1% (w/v) aqueous sodium-citrate solution and diH$_2$O. The tests were performed on substrates having a period of 1 μm (corresponding to field 2, see example 3). As is visible from FIG. 14, the adsorption from PBS did give the highest relevant signal increase; however, also marked signals upon adsorption of the antibody from other solutions were being observed. This could also be a consequence of the possible formation of a silver chloride layer, also described in example 6, which has a positive influence on the enhancement effect.

The invention claimed is:

1. A method for enhancing the fluorescence of one or several fluorescent molecules,
comprising:
providing a substrate that comprises a solid polymer carrier having a plurality of recesses separated from each other,
wherein the recesses in the plurality of recesses have a depth of 0.1 μm to 5 μm,
wherein the solid polymer carrier is coated at least in part by at least one metal layer comprising silver or an alloy thereof,
wherein the at least one metal layer has a thickness ranging from 10 nm to 60 nm;
positioning the one or several fluorescent molecules in a spatial proximity of the substrate coated at least in part by the at least one metal layer; and
exciting the one or several fluorescent molecules with light at a suitable wavelength,
thereby enhancing the fluorescence of the one or several fluorescent molecules.

2. The method according to claim 1, wherein the recesses in the plurality of recesses have a distance to each other of 0.2 μm to 2.5 μm.

3. The method according to claim 1, wherein the recesses in the plurality of recesses have a length and a width, and wherein the ratio of the length to the width ranges from 2:1 to 1:2.

4. The method according to claim 1, wherein the recesses in the plurality of recesses have a length and a width, wherein the length is 0.1 μm to 2 μm, and the width is 0.1 μm to 2 μm.

5. The method according to claim 1, wherein the recesses in the plurality of recesses have an essentially round shape.

6. The method according to claim 1, wherein the at least one metal layer comprises more than one metal layer.

7. The method according to claim 1, wherein the at least one metal layer comprises an alloy comprising silver, indium and tin.

8. The method according to claim 1, wherein the solid polymer carrier comprises at least one material chosen from thermoplastic polymers and polycondensates.

9. The method according to claim 8, wherein the thermoplastic polymers are chosen from polyolefins, vinyl polymers, styrene polymers, polyacrylates, polyvinyl carbazol, polyacetal, and fluoro-plastics.

10. The method according to claim 8, wherein the polycondensates are chosen from thermoplastic polycondensates, duroplastic polycondensates, and polyadducts.

11. The method according to claim 8, wherein the solid polymer carrier comprises one or more organic additives, inorganic additives, organic fillers, inorganic fillers, or a combination thereof.

12. The method according to claim 1, wherein the substrate further comprises part of a capillary tube, a microtiter plate, a microfluidic chip, an assay strip, a carrier for fluorescence microscopy, a sensor array, or an optical detector field.

13. The method according to claim 1, wherein the at least one metal layer comprises one or more molecules for the direct and/or indirect bonding of fluorescent molecules.

14. The method according to claim 13, wherein the one or more molecules for the direct and/or indirect bonding of fluorescent molecules are chosen from antibodies, antibody fragments, Fab fragments, F(ab)'2 fragments, scFv fragments, nucleic acids, enzymes, lipids, virus particles, aptamers, and combinations thereof.

15. The method according to claim 3, wherein the ratio of the length to the width is 1:1.

16. The method according to claim 11, wherein the one or more organic additives, inorganic additives, organic fillers, inorganic fillers, or a combination thereof is chosen from $TiO_2$, glass, carbon, colour pigments, lipids, waxes, and combinations thereof.

17. A method for quantifying at least one analyte in a sample, comprising:
 a) directly or indirectly labelling the at least one analyte with at least one fluorophore to produce at least one labelled analyte,
 b) applying the at least one labelled analyte onto a substrate that comprises
 a solid polymer carrier having a plurality of recesses separated from each other,
 wherein the recesses in the plurality of recesses have a depth of 0.1 µm to 5 µm,
 wherein the solid polymer carrier is coated at least in part by at least one metal layer comprising silver or an alloy thereof,
 wherein the at least one metal layer has a thickness ranging from 10 nm to 60 nm;
 wherein the at least one fluorophore is positioned in a spatial proximity of the solid polymer carrier coated at least in part by the at least one metal layer;
 c) exciting the at least one fluorophore by irradiation of the substrate using light at an appropriate wavelength, and
 d) measuring the fluorescence from the at least one fluorophore to quantify the at least one analyte in the sample.

18. The method according to claim 17, wherein the at least one fluorophore has an excitation wavelength in the range of 360 to 780 nm.

19. The method according to claim 17, wherein the at least one fluorophore has an emission wavelength in the range of 410 to 800 nm.

20. The method according to claim 17, wherein the at least one fluorophore is chosen from methoxy coumarin, amino coumarin, fluorescein isothiocyanate (FITC), phycoerythrin (PE), tetramethyl rhodamine isothiocyanate (TRITC), and rhodamine.

21. The method according to claim 17, wherein the indirectly labelling of the analyte with at least one fluorophore comprises contacting the at least one analyte with a fluorophore-labelled and analyte-binding molecule.

22. The method according to claim 21, wherein the fluorophore-labelled and analyte-binding molecule is chosen from antibodies, antibody fragments, Fab fragments, F(ab)'2 fragments, scFv fragments, nucleic acids, enzymes, lipids, virus particles, aptamers, and combinations thereof.

* * * * *